(12) United States Patent
Hanson

(10) Patent No.: US 10,639,160 B2
(45) Date of Patent: May 5, 2020

(54) PEEK FEMORAL COMPONENT WITH SEGMENTED TI FOAM IN-GROWTH

(71) Applicant: Howmedica Osteonics Corp., Mahwah, NJ (US)

(72) Inventor: Keenan Michael Hanson, Sloatsburg, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 39 days.

(21) Appl. No.: 15/682,872

(22) Filed: Aug. 22, 2017

(65) Prior Publication Data

US 2018/0055642 A1 Mar. 1, 2018

Related U.S. Application Data

(60) Provisional application No. 62/378,914, filed on Aug. 24, 2016.

(51) Int. Cl.
| | | |
|---|---|---|
| *A61F 2/38* | (2006.01) | |
| *A61L 27/56* | (2006.01) | |
| *A61F 2/30* | (2006.01) | |
| *A61F 2/36* | (2006.01) | |

(52) U.S. Cl.
CPC ........ *A61F 2/30767* (2013.01); *A61F 2/3094* (2013.01); *A61F 2/36* (2013.01); *A61F 2/38* (2013.01); *A61L 27/56* (2013.01); *A61F 2/3859* (2013.01); *A61F 2002/30004* (2013.01); *A61F 2002/3007* (2013.01); *A61F 2002/3092* (2013.01); *A61F 2002/30878* (2013.01); *A61F 2002/30971* (2013.01)

(58) Field of Classification Search
CPC ...... A61F 2/38; A61F 2/3858; A61F 2/30767; A61F 2002/30065; A61F 2002/30457; A61F 2002/30973
See application file for complete search history.

(56) References Cited

U.S. PATENT DOCUMENTS

| | | | |
|---|---|---|---|
| 4,205,400 A | 6/1980 | Shen et al. | |
| 4,355,429 A | 10/1982 | Mittelmeier et al. | |
| 4,778,473 A | 10/1988 | Matthews et al. | |
| 5,080,674 A * | 1/1992 | Jacobs | A61F 2/30734 623/20.17 |
| 5,236,457 A | 8/1993 | Devanathan | |
| 5,370,696 A | 12/1994 | Jamison et al. | |

(Continued)

FOREIGN PATENT DOCUMENTS

EP 2319462 A1 5/2011

OTHER PUBLICATIONS

European Search Report from EP 17 18 7568, dated Jan. 26, 2018, pp. 1-3.
U.S. Appl. No. 15/137,601, filed Apr. 25, 2016.

*Primary Examiner* — Brian A Dukert
(74) *Attorney, Agent, or Firm* — Lerner, David, Littenberg, Krumholz & Mentlik, LLP

(57) ABSTRACT

A medical implant includes a body and a porous structure attached to the body. A boss integral with the body extends outwardly from a surface of the body. The porous structure has a surface that cooperates with the boss of the body to prevent pullout of the body from the porous structure. In fabricating the medical implant, the body and the porous structure are formed separately and subsequently secured together.

14 Claims, 11 Drawing Sheets

(56) References Cited

U.S. PATENT DOCUMENTS

| | | |
|---|---|---|
| 5,387,243 A | 2/1995 | Devanathan |
| 5,973,222 A | 10/1999 | Devanathan et al. |
| 6,049,054 A | 4/2000 | Panchison et al. |
| 6,364,910 B1 | 4/2002 | Shultz et al. |
| 6,740,186 B2 | 5/2004 | Hawkins et al. |
| 6,945,448 B2 | 9/2005 | Medlin et al. |
| 7,115,131 B2 | 10/2006 | Engh et al. |
| 7,520,901 B2 | 4/2009 | Engh et al. |
| 7,537,664 B2 | 5/2009 | O'Neill et al. |
| 7,572,295 B2 | 8/2009 | Steinberg |
| 7,896,922 B2 | 3/2011 | Engh et al. |
| 7,918,382 B2 | 4/2011 | Charlebois et al. |
| 8,070,821 B2 | 12/2011 | Roger |
| 8,191,760 B2 | 6/2012 | Charlebois et al. |
| 8,333,805 B2 | 12/2012 | Williams, III et al. |
| 8,350,186 B2 | 1/2013 | Jones et al. |
| 8,430,930 B2 | 4/2013 | Hunt |
| 8,545,569 B2 | 10/2013 | Fitz et al. |
| 8,690,945 B2 | 4/2014 | Fitz et al. |
| 8,696,328 B2 | 4/2014 | Yang |
| 8,814,946 B2 | 8/2014 | Steinberg |
| 8,828,081 B2 | 9/2014 | Boyden et al. |
| 8,845,739 B2 | 9/2014 | Boyden et al. |
| 8,845,740 B2 | 9/2014 | Boyden et al. |
| 8,882,847 B2 | 11/2014 | Burdulis, Jr. et al. |
| 8,945,230 B2 | 2/2015 | Lang et al. |
| 8,979,938 B2 | 3/2015 | Linares |
| 8,985,430 B2 | 3/2015 | Charlebois et al. |
| 9,089,434 B2 | 7/2015 | Eli |
| 9,114,012 B2 | 8/2015 | Wogoman |
| 9,162,008 B2 | 10/2015 | Serafin, Jr. et al. |
| 9,180,015 B2 | 11/2015 | Fitz et al. |
| 9,186,254 B2 | 11/2015 | Fitz et al. |
| 2004/0191106 A1 | 9/2004 | O'Neill et al. |
| 2006/0147332 A1 | 7/2006 | Jones et al. |
| 2006/0235542 A1 | 10/2006 | Hodorek et al. |
| 2007/0142914 A1 | 6/2007 | Jones et al. |
| 2010/0312348 A1 | 12/2010 | Wang et al. |
| 2011/0012280 A1 | 1/2011 | Deslauriers et al. |
| 2012/0156069 A1 | 6/2012 | Yang |
| 2012/0185053 A1 | 7/2012 | Berger |
| 2013/0020733 A1 | 1/2013 | Berger |
| 2013/0268085 A1 | 10/2013 | Dong et al. |
| 2014/0277529 A1* | 9/2014 | Stalcup ............... A61F 2/38  623/20.16 |
| 2014/0296929 A1 | 10/2014 | Stacey |
| 2015/0134063 A1 | 5/2015 | Steinmann et al. |
| 2016/0113770 A1 | 4/2016 | Early et al. |
| 2017/0027707 A1 | 2/2017 | Cremascoli |

\* cited by examiner

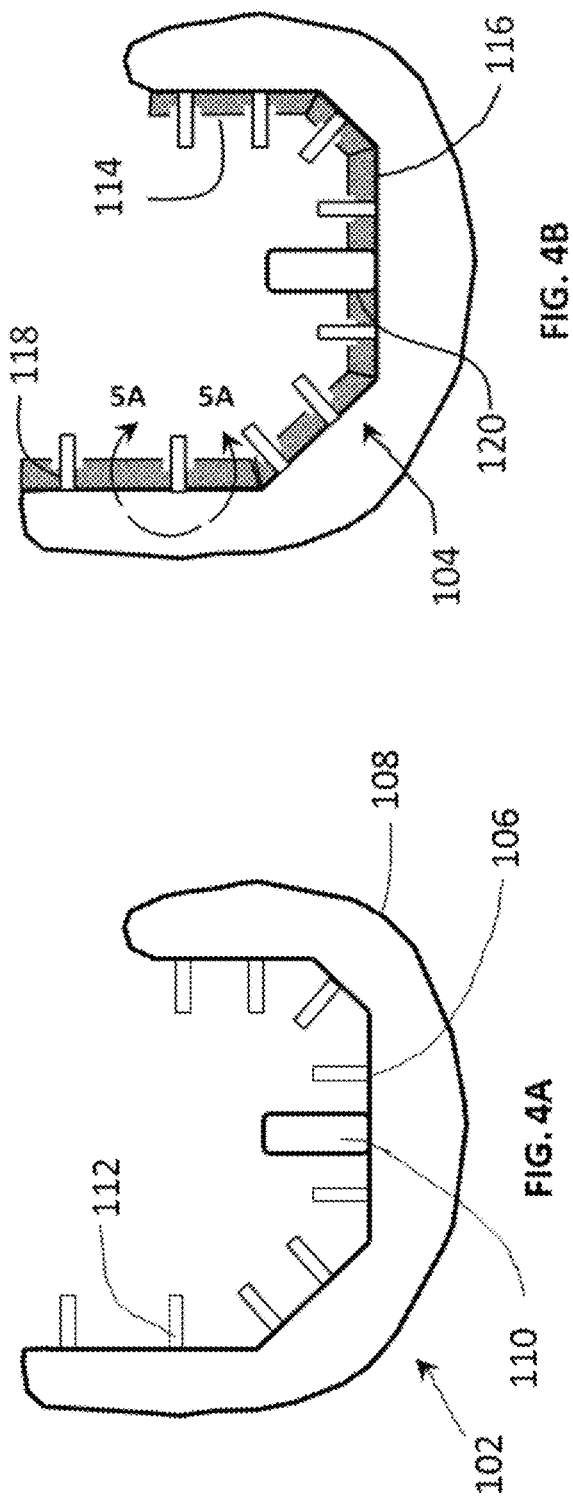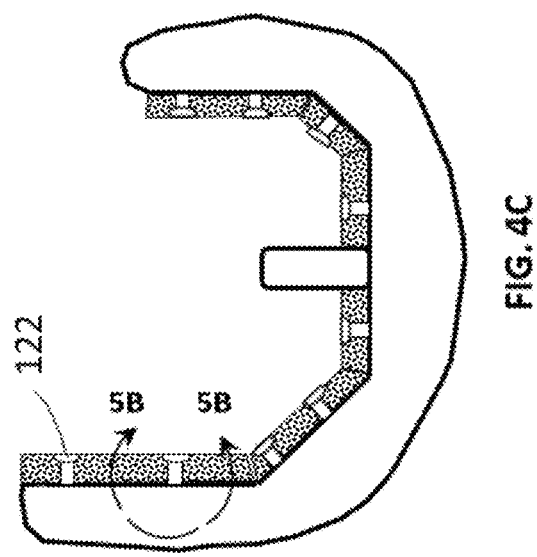

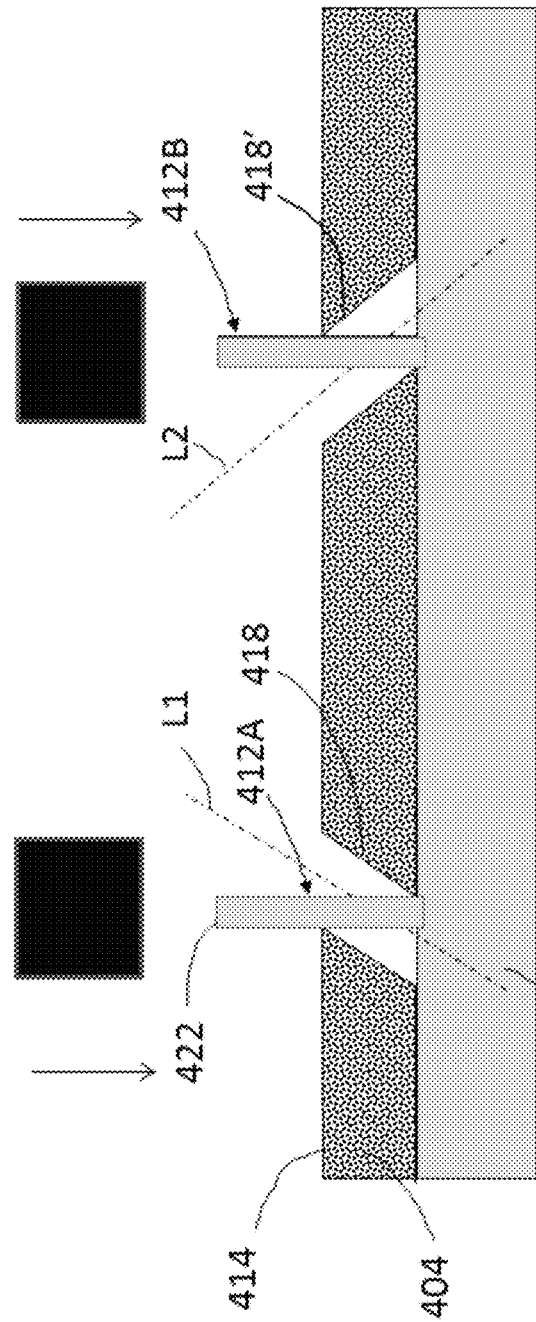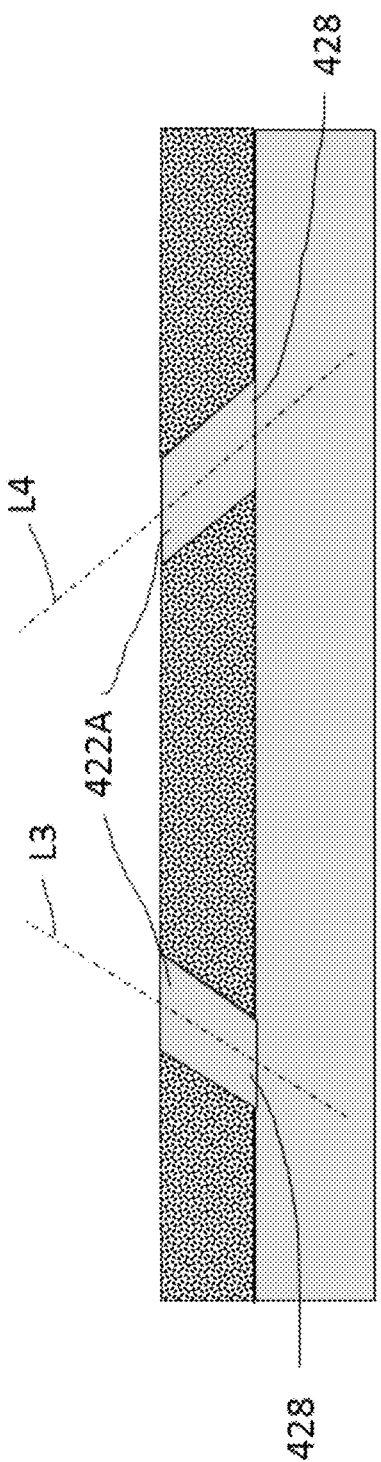
FIG. 8A
FIG. 8B

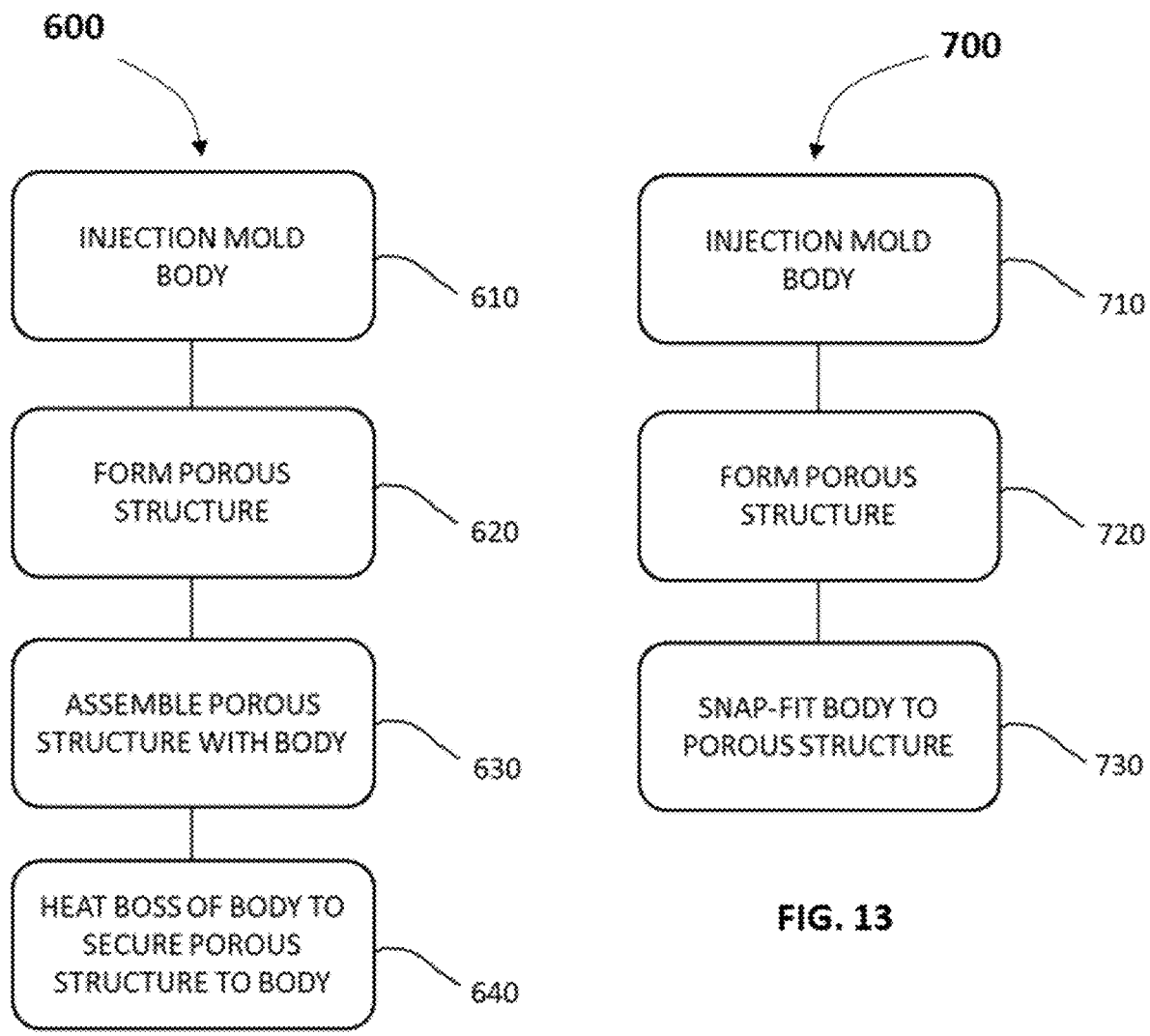

PEEK FEMORAL COMPONENT WITH SEGMENTED TI FOAM IN-GROWTH

CROSS-REFERENCE TO RELATED APPLICATION

The present application claims the benefit of the filing date of U.S. Provisional Patent Application No. 62/378,914, file on Aug. 24, 2016, the disclosure of which is hereby incorporated herein by reference.

FILED OF THE INVENTION

The present invention relates to a medical implant for bone and a method for its fabrication, and in particular relates to a composite medical implant for bone and a method for its fabrication.

BACKGROUND OF THE INVENTION

Bone-contacting implants preferably have an elastic modulus, i.e., stiffness, which is the same as a recipient bone to ensure proper operation and durability. An implant with insufficient stiffness will be unable to withstand the physiological loads, possibly leading to implant failure. However, excessive stiffness in an implant will lead to stress shielding and could result in bone resorption. Stress shielding leads to bone loss when excessively stiff implants prevent natural loading on the recipient bone. Implants made from relatively stiff polymer materials such as polyetheretherketone ("PEEK") are commonly used with bone because the elastic modulus of PEEK is similar to cortical bone.

Implants, such as femoral components for partial or total knee replacements, are commonly attached to the recipient bone by long anchor pins and further secured to the bone by bone cement such as polymethylmethacrylate compositions. However, bone cement bonding has been observed to fail in some instances. Porous bone contacting surfaces, fabricated by suitable biocompatible metals such as titanium, have been used on implants to provide improved fixation by allowing bone tissue to grow into the porous structure and secure the connection.

A composite implant made of a PEEK body and a porous titanium core will simultaneously provide sufficient strength and adequate bone fixation. However, the stiffness of titanium is much greater than cortical bone, thus making it difficult to maintain an overall implant stiffness in line with cortical bone. Furthermore, polymeric components, such as those made of PEEK, are commonly formed by injection molding which requires additional rework to parts and molds when injection-molding such components around stiff cores and occasionally even leads to deformation of such cores.

SUMMARY OF THE INVENTION

In accordance with an aspect of the present invention, an implant may include a body and a porous structure attached to the body. One or more surfaces integral with and defined by the body may be above a surface of the porous structure to prevent pullout of the body from the porous structure. In some arrangements, any such surface may be part of a boss of the body that may extend through the porous structure.

In accordance with another aspect of the present invention, an implant may include a body with a boss extending from a surface of the body and a porous structure attached to the body in cooperation with the boss. In an arrangement, the boss may extend at an angle with respect to the surface of the body to cooperate with a corresponding hole through the porous structure to prevent pullout of the porous structure from the body. In another arrangement, the boss may have a first portion and a thicker second portion away from the body configured to cooperate with a corresponding hole in the porous structure such that the porous structure is inseparable from the body. The porous structure may be a single monolithic construct or an assembly of a plurality of structures of different shapes and dimensions. The body may be made by any suitable biocompatible material which possess sufficient strength and rigidity, whereas the porous structure may be made of titanium or similar materials to allow bone tissue to grow into the porous structure.

Another aspect of the present invention is a process of fabricating an implant similar to the implant described above. In one step of this process, a body may be formed. In another step of this process, a porous structure may be formed. The body may be formed through an injection molding process. The porous structure may be formed through an additive manufacturing process. In another step of the process, the porous structure may be secured to the body by placing the porous structure on the body to allow the boss to extend through the hole of the porous structure and subsequently melting the extended boss such that a portion of the melted boss extends over the porous structure. In this manner, the body may partially surround the porous structure to prevent pullout of the porous structure from the body. In some arrangements, the boss may be exposed on a bone-contacting surface of the porous structure when the porous structure is attached to the body. In some other arrangements, the boss may lie at least partially within the porous structure.

In some arrangements of the present invention, the porous structure of the implant may include a plurality of structures, which may be of different shapes and dimensions. Each of these structures may be provided with holes or other expedients so that the structures may be attached to or otherwise associated with a body having a boss. For example, in certain arrangements, the boss may include a flexible flange that may be pushed into a corresponding recess with an undercut in the porous structure to secure the porous structure to the body.

In accordance with another aspect of the present invention, an implant may include a body and a porous structure attached to the body. The body may have opposing first and second surfaces. The first surface may have a boss extending outwardly from the first surface. The boss may be integral with the body. The porous structure may have a surface that cooperates with the boss of the body to prevent pullout of the boss from the porous structure. In this manner, the porous structure may be prevented from being separated from the body.

In some arrangements, the boss may define a longitudinal axis that extends at an oblique angle to the first surface to prevent pullout of the boss.

In some arrangements, the porous structure may be a monolithic construct. In other arrangements, the porous structure may include two or more porous segments. In some such arrangements, one or more of the porous segments may be planar.

In some arrangements, the first surface may be an inner surface of the body having one or more planar surfaces.

In some arrangements, the body may be partially or fully flexible. In some such arrangements, the body may be made of a flexible polymer such as, but not limited to, PEEK, polyaryletherketones ("PAEK") and ultra-high molecular weight polyethylene ("UHMWPE). The porous structure may be fabricated from, but is not limited to being fabricated from, any of titanium, titanium alloys, stainless steel, cobalt chrome, tantalum and niobium.

In some arrangements, the boss may not extend above a top surface of the porous structure. In some such arrangements, the top surface of the porous structure may be a bone-contacting surface.

In accordance with another aspect of the present invention, an implant may include a body and a porous structure attached to the body. The body may have opposing first and second surfaces. The first surface of the body may have a boss that may extend outwardly from the first surface. The boss may be integral with the body. The boss may have a first portion and a second portion wider than the first portion. The porous structure may include a recess. The recess may have a shape and dimensions substantially corresponding to the shape and dimensions of the boss of the body. The boss of the body may be inserted into the porous structure such that the boss prevents pullout of the boss of the body from the porous structure. In this manner, the porous structure may be prevented from being separated from the body.

In some arrangements, the second portion of the boss may form any of a dome stake, a rosette stake, and a hollow stake in cooperation with the top surface of the porous structure to prevent pullout of the body from the porous structure.

In some arrangements, the porous structure may include at least one hole and a counter bore. The boss of the body may extend through the hole. The second portion of the boss may extend within the counterbore of the hole. In some arrangements, the porous structure may include a recess to receive the boss of the body to prevent pullout of the body from the porous structure.

In accordance with another aspect of the present invention, an implant may be fabricated. In a step of the process, a body is formed. The body may be formed to have opposing first and second surfaces and may have a boss that extends outwardly from the first surface. In another step of the process, a porous structure is formed. The porous structure may be configured to be placed on the first surface of the body, which may be an inner surface of the body. In another step of the process, the porous structure is secured with the boss of the formed body. In this manner, the boss of the body may prevent pullout of the body from the porous structure.

In some arrangements, the body may be formed by injection molding.

In some arrangements, the porous structure may be formed by any additive manufacturing process. In a step of the additive manufacturing process, a first layer of a metal powder may be deposited onto a substrate. In another step, a beam may be scanned so as to melt the metal powder at predetermined locations to form a portion of a plurality of porous geometries. The porous geometries may be in the form of predetermined unit cells and may have a plurality of struts with a length and a cross-section. In another step, at least one additional layer of metal powder may be deposited onto the first layer. In another step, the step of scanning a beam may be repeated for at least some of the additional deposited metal powder layers in order to continue forming the porous geometries.

In some such arrangements, the porosity within the porous structure may be varied during the additive manufacturing process. Such porosity may be varied by (i) forming a unit cell in one metal powder layer having a different shape from a unit cell within a successive metal powder layer. Such porosity may be varied by forming a unit cell in one metal powder layer having at least one strut having a different dimension from a corresponding strut of a unit cell of the same shape within a successive metal powder layer. Such porosity may be varied by applying a random perturbation in any direction to vertices of the unit cells to randomize the geometry of the unit cells. Any or all of these process steps may be utilized to fabricate the porous structure.

In some such arrangements, each of the scanning steps may form portions of a plurality of segments forming portions of the porous structure. The segments may have different dimensions from each other. Such segments may be formed of the porous geometries.

In some arrangements, the porous geometries may be fabricated to vary porosity within the porous structure.

In some arrangements, during the securing step, a first surface of the porous structure may be placed against the first surface of the body such that the boss extends through a hole of the porous structure. In this manner, a first portion of the boss is within the hole and a second portion of the boss extends over a second surface of the porous structure remote from the first surface. In some such arrangements, during the securing step, the second portion of the boss may then be melted, e.g., by thermoplastic staking, such that the melted second portion fills the counterbore to secure the porous structure to the body. A porous structure made of multiple segments may also be attached to the body, such as to the first surface of the body, in the same manner.

In some arrangements, during the securing step, the boss of the body may be inserted through a recess of the porous structure such that a flange at an end of the boss extends through an undercut at an end of the recess in the porous structure to secure the porous structure to the body. In some such arrangements, during the securing step, the body is flexed to allow the flange to be inserted into the undercut.

BRIEF DESCRIPTION OF THE DRAWINGS

A more complete appreciation of the subject matter of the present invention and the various advantages thereof can be realized by reference to the following detailed description, in which reference is made to the following accompanying drawings:

FIGS. 4A-4C are cross-sectional elevation views of the implant of FIG. 1 illustrating sequential steps for securing the porous structure of FIG. 2 to the body of FIG. 2 in accordance with another embodiment;

FIGS. 8A and 8B are cross-sectional elevation views illustrating aspects of a staking process for fabricating the implant of FIGS. 7A-7C in accordance with another embodiment;

FIG. 12 is a diagrammatic view of a process for fabricating an implant in accordance with an embodiment;

FIG. 13 is a diagrammatic view of a process for fabricating an implant in accordance with another embodiment.

DETAILED DESCRIPTION

Figure 1:
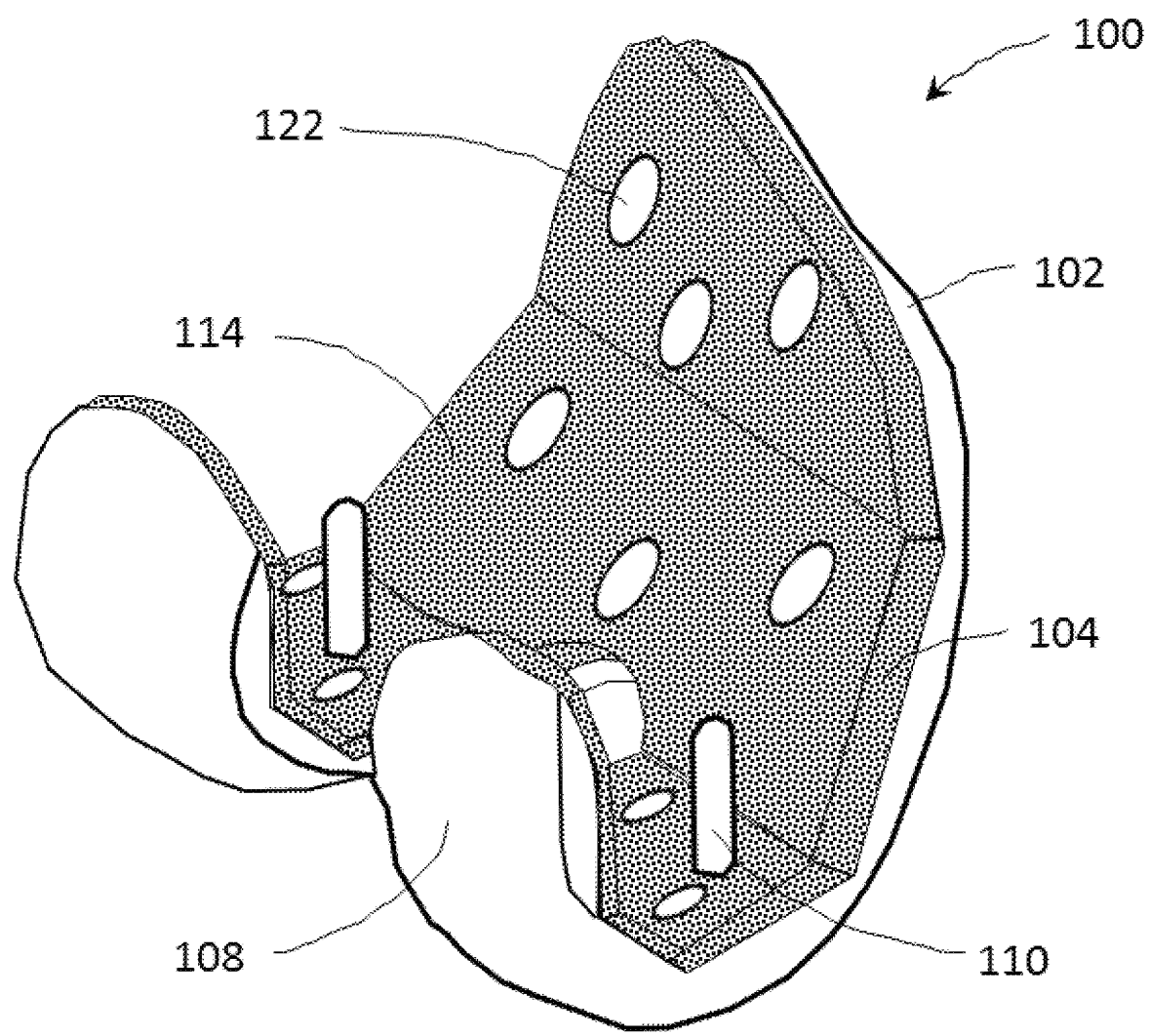
FIG. 1 is a perspective view of an implant in accordance with an embodiment.
Figure 2:
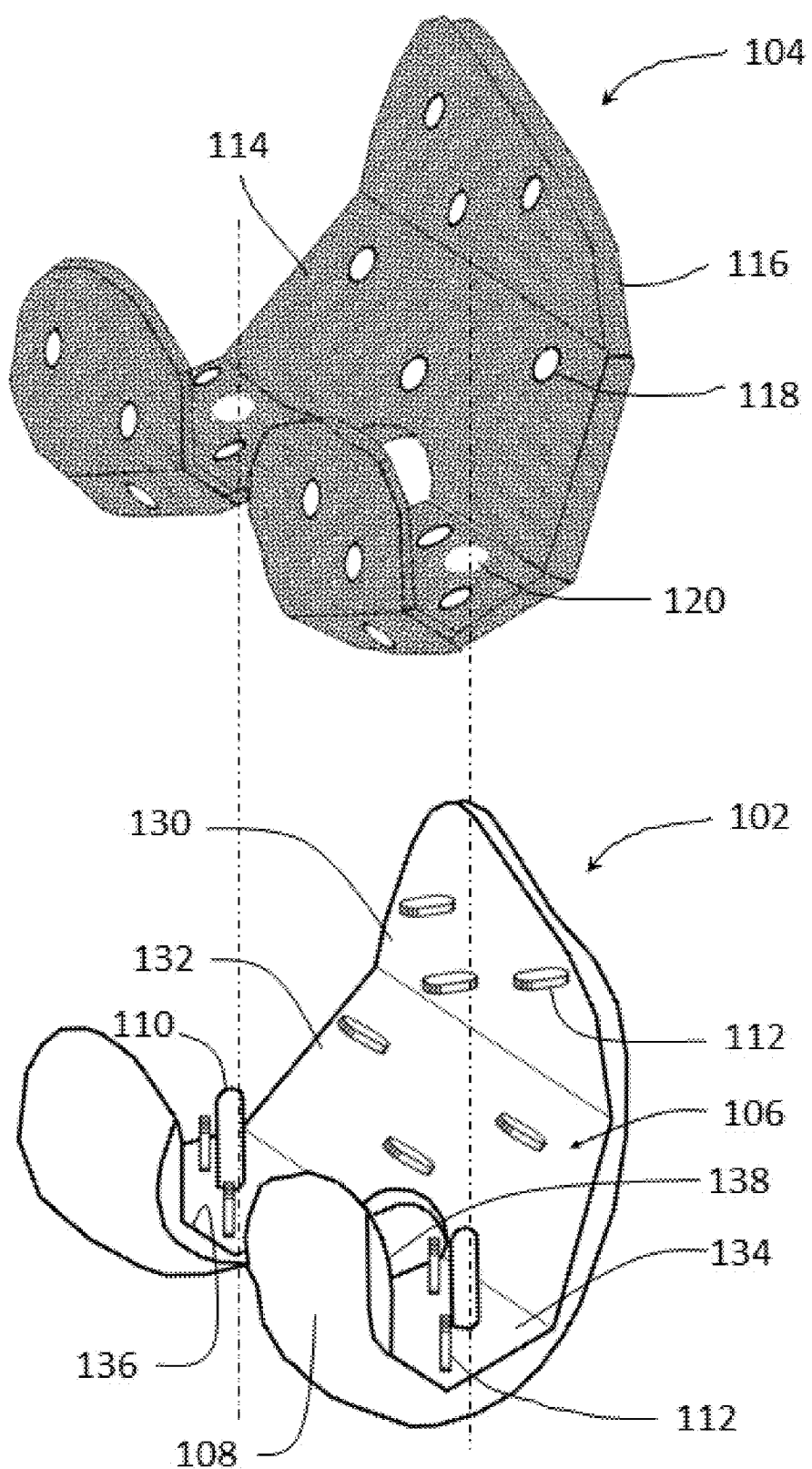
FIG. 2 is an exploded perspective view of the implant shown in FIG. 1.

As defined herein and in the claims, the term "integral with" means "monolithic with and inseparable from." Referring to FIGS. 1 and 2, implant 100, which as shown may be a femoral component for a distal end of a femur, includes body 102 and porous structure 104. Whereas a femoral component is described here, the present invention can be utilized for other implants such as, but not limited to, hip implants, spinal implants and dental implants. Body 102 has a mating first surface 106 on which porous structure 104 may be placed. In some instances, such as in the example shown, articulating second surface 108 may contact or otherwise engage with another prosthesis, including but not limited to a tibial base plate. In other instances, second surface 108 may contact or otherwise engage with a bone, including but not limited to a tibia. Such contacts or engaging may take on any suitable arrangement for the particular application. In the illustrated preferred embodiment, first surface 106 has two securing posts 110 which may aid in the fixation of implant 100 to a recipient bone. A plurality of tabs or bosses 112 extend from first surface 106 in this embodiment. Bosses 112 are integral with body 102. As in the example of the femoral component shown, bosses 112 may extend from one or more surfaces 106 forming angles with each other and be any of parallel with, skew with, and set to form an angle with at least some of the other bosses. Consequently, bosses 112 may extend in two or more directions or even in multiple directions relative to inner surface 106 to increase fixation between body 102 and porous structure 104. It is noted that surface 106 may be considered to be made up in some examples of a plurality of surfaces corresponding to anterior surface 130, anterior chamfer surface 132, distal surface 134, posterior chamfer surface 136 and posterior condyle surface 138. Bosses 112 may extend from any or all of such surfaces to increase fixation between body 102 and porous structure 104. In the illustrated preferred embodiment, bosses 112 are integral to body 102 such that the bosses are inseparable from the body and are used to anchor or otherwise associate porous structure 104 to body 102.

As shown in FIG. 2, porous structure 104 is made of a single construct. Porous structure 104 has a bone-contacting surface 114 and an opposing surface 116 in contact with second surface 108 of body 102. A plurality of holes 118 extend through porous structure 104 and are each dimensioned and positioned in the preferred embodiment to receive a corresponding boss 112 of body 102. A pair of holes 120 also extends through porous structure 104 and are dimensioned and positioned to receive securing posts 110.

Figure 3:
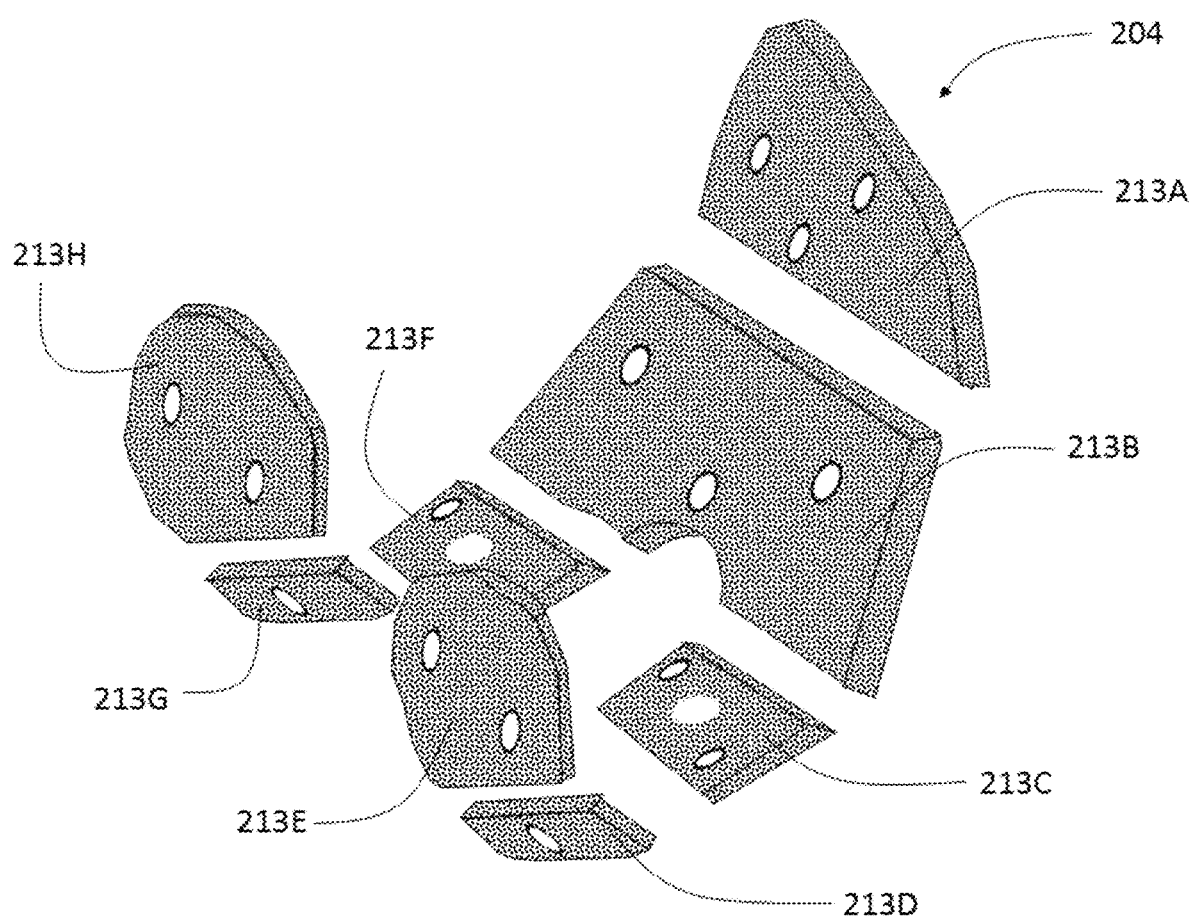
FIG. 3 is an exploded perspective view of a porous structure of the implant shown in FIG. 1 in accordance with another embodiment.

Porous structure 204 shown in FIG. 3 is substantially similar to porous structure 104 with the exception that porous structure 204 includes a plurality of porous structures 213A-213H for placement onto first surface 106 of body 102 in lieu of porous structure 104. In this example, porous structure 204 includes eight separate porous surfaces that may be attached to respective planar or other bone cuts of a resected distal femur (not shown). Other embodiments may have additional or fewer porous structure segments to facilitate greater flexibility in combining a flexible outer body with a rigid porous structure, i.e., reducing or increasing the rigid porous structures based on the overall stiffness required for femoral implant 100. In general, increasing the number of segments reduces the overall stiffness while decreasing the number of segments increases the overall stiffness of the implant. The resulting interiorly facing surface of implant 100, i.e., the surface facing in the same direction as surface 106 of body 102 and as surface 114 of porous structure 104, is substantially defined by surface 114. However, other arrangements may have segmented porous structures at only specific locations upon the body of the implant such that the resulting interiorly facing surface of the implant 100 is defined in part by a porous structure and in part by surface 106 of body 102 or perhaps even some other structure in association with surface 106. The plurality of porous structures shown in this embodiment may be made in the manner disclosed by U.S. Pat. No. 8,350,186, the disclosure of which is hereby incorporated by reference herein as if fully set forth herein.

As shown in FIGS. 4A-4C, porous structure 104 may be secured to body 102 through sequential steps. Bottom surface 116 of porous structure 104 is placed on inner first surface 106 of body 102 such that bosses 112 and securing posts 110 pass through corresponding holes 118 and 120, respectively, as shown in FIG. 4B.

Figure 5A:
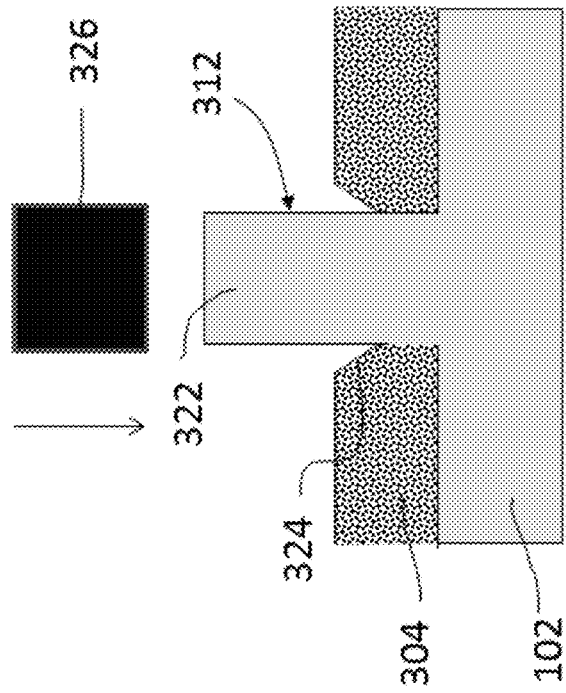
FIGS. 5A and 5B are elevation views illustrating aspects of a staking process for fabricating the implant of FIG. 1 in accordance with another embodiment.

As shown in FIG. 5A, boss 112 extends through corresponding hole 118 in which top portion 122 of the boss protrudes beyond top surface 114 of porous structure 104. Heated thermal tip 126 is then brought into contact with boss 112 such that top portion 122 melts and fills the volume of counterbore 124 provided at an end of hole 118. Top portion 122 then solidifies to form head 122A that is thicker than bottom portion 128 of boss 112, thereby securing porous structure 104 to body 102, as shown in the example of FIG. 4C.

Figure 5B:
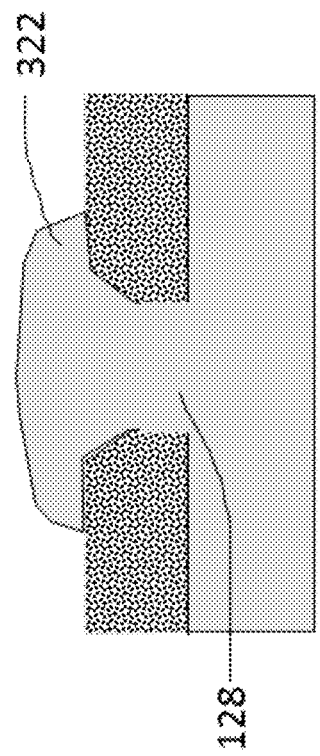
Figure 6A:
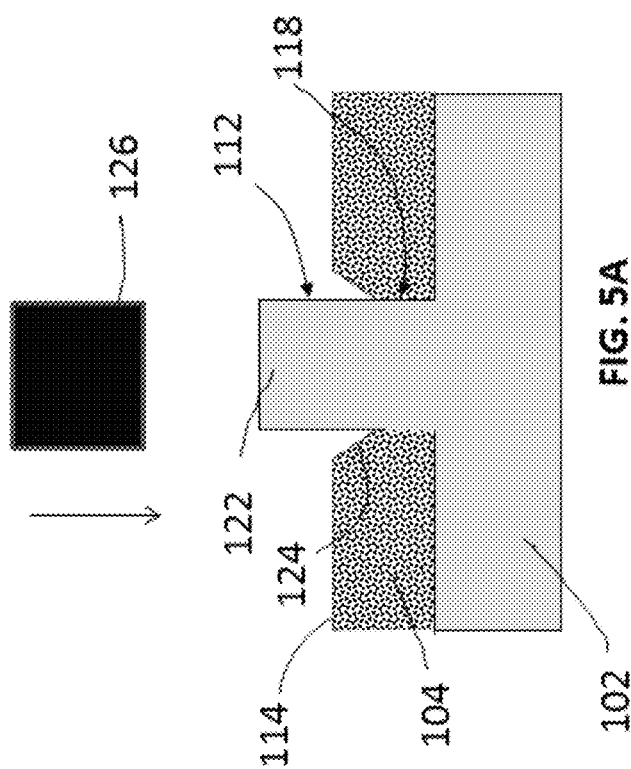
FIGS. 6A and 6B are cross-sectional elevation views illustrating aspects of a staking process for fabricating the implant of FIG. 1 in accordance with another embodiment.
Figure 6B:
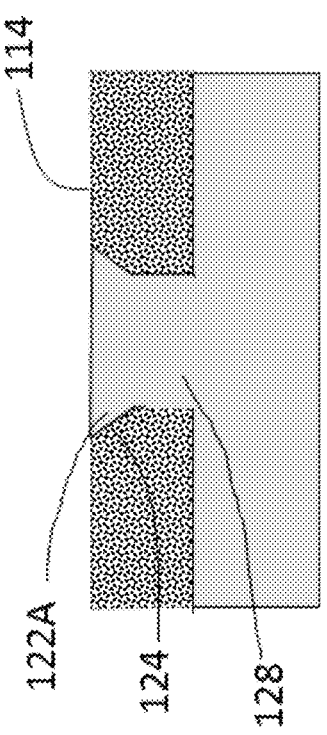
Figure 7A:
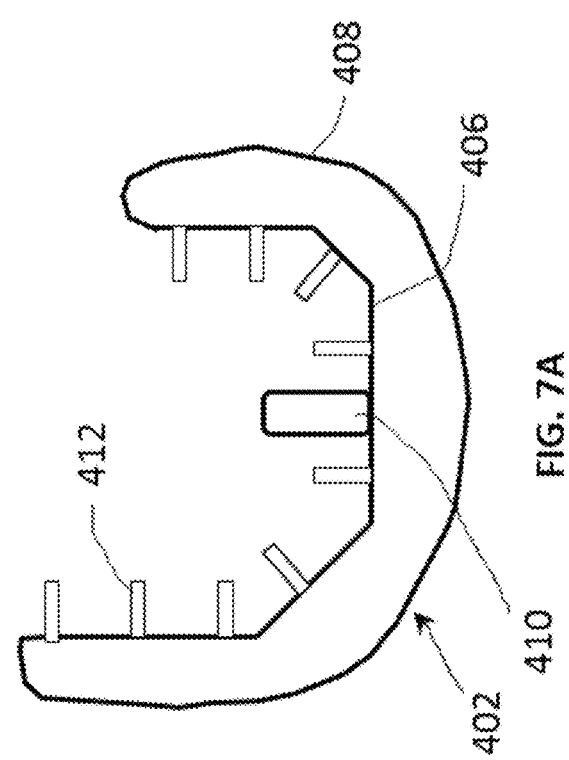
FIGS. 7A-7C are cross-sectional elevation views of an implant in accordance with another embodiment illustrating sequential steps for securing a porous structure to a body.
Figure 7B:
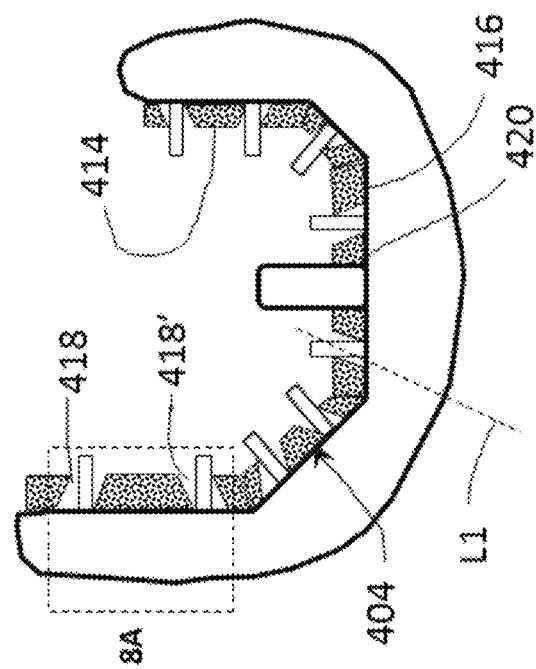
Figure 7C:
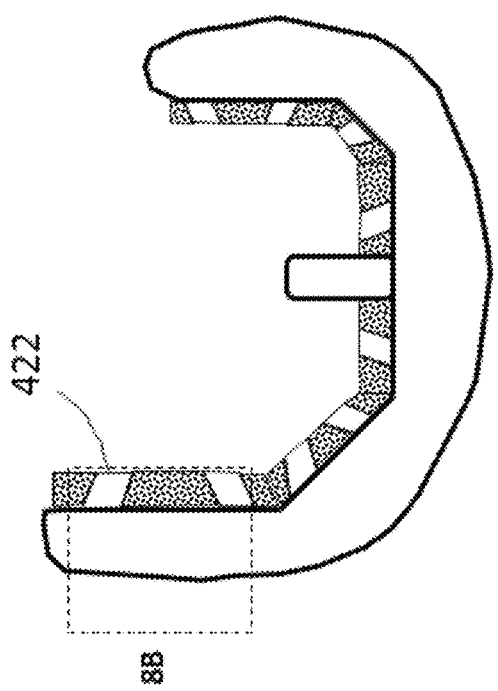

The volume of counterbore 124 and the volume of protruding top portion 122 of boss 112 may be adjusted to achieve a desired surface finish if desirable. As shown in the example of a flush finish in FIG. 5B, top surface 122 of boss 112 is flush with top surface 114 of porous structure 104. In this arrangement, the volume of counterbore 124 is the same or substantially the same as the volume of boss 112 protruding above top surface 114. In an alternative arrangement shown in FIGS. 6A and 6B, the volume of counterbore 324 of porous structure 304 is less than protruding top portion 322 of boss 312. In this manner, melting the top portion with heated thermal tip 326 results in a rosette stake finish as shown in FIG. 6B. In other arrangements, other known surface finishes such as a knurled stake, a hollow stake, and a dome stake may be achieved by adjusting the counterbore volume with respect to the volume of the top portion of the boss. In another alternative arrangement, porous structure 104 may have a porosity such that a boss, such as boss 112, of a body may interdigitate into the porous structure when the boss is melted to thereby attach the body to the porous structure. Interdigitating this boss directly with this porous structure may not require any holes or recesses to be in the porous structure. In still other embodiments, a porous structure may be heated at predetermined locations to melt and pool into corresponding holes or recesses provided in a body. In this manner, the porous structure may be attached to the body upon cooling and solidification within the holes or recesses in the body.

Referring now to FIGS. 7A-8B, there is shown sequential steps to secure body 402 to porous structure 404 in forming implant 400. As shown, porous structure 404 includes a plurality of holes 418, 418'. As shown in FIG. 7B, holes 418, 418' are inclined with respect to their interface with inner surface 406 of body 402 such that longitudinal axes L1, L2 defined by the holes form different angles with inner surface of the body where the axes intersect. When implant 400 is assembled, bottom surface 416 of porous structure 404 rests on inner surface 406 of body 402 such that top portion 422 of bosses 412 and securing post 410 pass through respective holes 418, 418' and 420 as shown in FIG. 7B and FIG. 8A.

As best shown in FIGS. 8A and 8B, bosses 412 of body 402 are melted into holes 418 of porous structure 404. Heat staking or other similar methods may be utilized to melt bosses 412. In this arrangement, melted bosses 412A, 412B completely fill and solidify in respective holes 418, 418'. As in the example shown in FIG. 8B, upper end portion 422A and lower end portion 428 of melted boss 412A, 412B have substantially the same dimensions. Other arrangements may include upper and lower ends of different dimensions. When melted bosses 412A, 412B completely fill respective holes 418, 418', melted bosses 412A, 412B are inclined such that longitudinal axes L3, L4 defined by melted bosses 412A, 412B are collinear with longitudinal axes L1, L2 of respective holes 418, 418.' This inclined arrangement of bosses 412 best shown in FIG. 8B facilitates the fixation of body 402 to porous structure 404 to prevent pullout of porous structure 404 from body 402. As in the example shown, in some arrangements, longitudinal axes L1, L2 defined by holes 418, 418', respectively, form equal and opposite angles with the inner surface 406 of body 402 where the longitudinal axes intersect the body.

As shown in FIGS. 9-11C, distal femoral implant 500 includes flexible body 502 and porous structure 504. Flexible body 502 may be made of a material such as certain of those set forth below, e.g., PEEK. In this embodiment, a plurality of bosses 512 extend from mating first surface 506 of body 502. Specifically, in this embodiment but not limiting, bosses 512 extend from inner surface 506 and flare outwardly to form a flange. Porous structure 504 is substantially similar to porous structure 104 with the notable exception that the porous structure includes recesses 532 having undercuts 534. In this example, recess 532 extend from bottom surface 516 of porous structure 504 and has undercut 534 at its end that does not extend to top surface 514 opposite the bottom surface of the porous structure. Thus, recesses 532 can be seen in FIG. 10 on the posterior side of the porous structure but not on the anterior side of the porous structure.

Figure 11B:
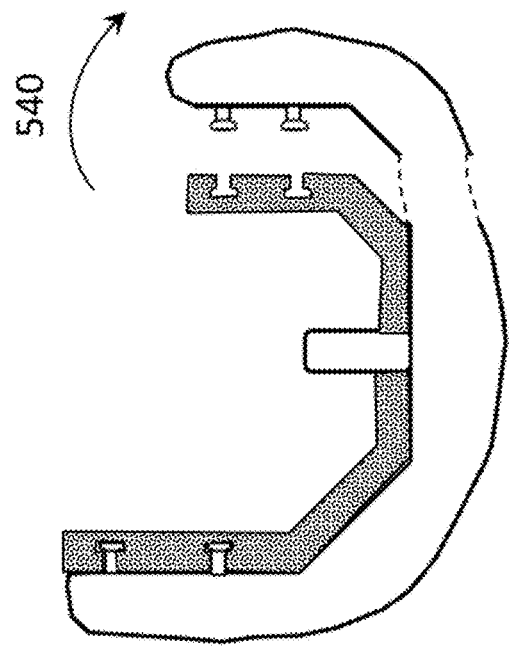
FIGS. 11A-11C are cross-sectional elevation views of the implant of FIG. 9 illustrating sequential steps for securing the porous structure of FIG. 10 to the body of FIG. 10 in accordance with another embodiment.
Figure 11C:
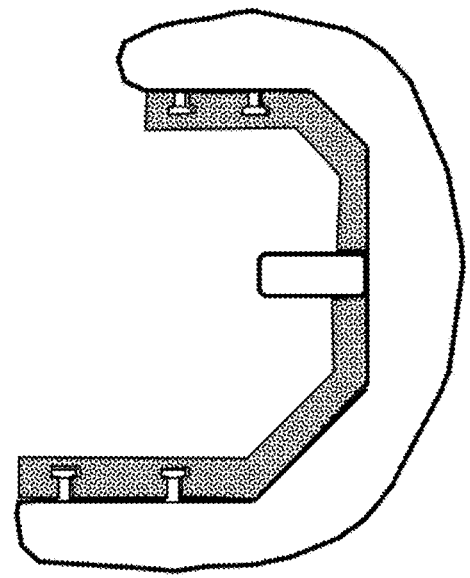
Figure 11A:
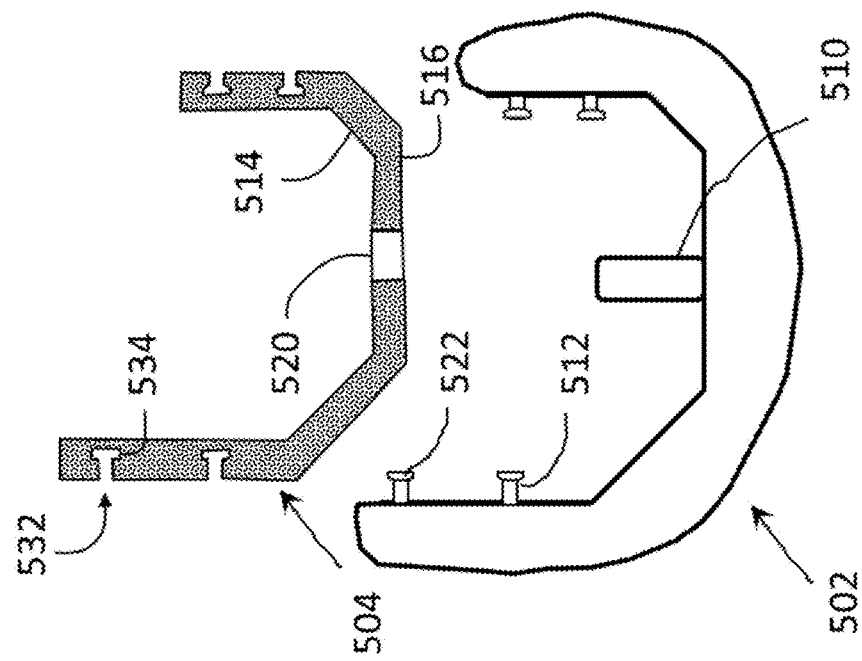

With reference to FIGS. 11A-11C, body 502 is secured to porous structure 504 through a series of sequential steps. As best shown in FIG. 11A, recess 532 is dimensioned to allow a flexible top portion 522 of boss 512, that is wider than recess 532, to be forced through the recess. The top portion 522 of boss 512 flares outwardly to form a flange, which constricts when pushed into the smaller recess 532. Upon reaching undercut 534, the flange of top portion 522 expands into the larger undercut space and thereby prevents boss 512 from separating from the porous structure. In this manner, each boss 512 may be pushed into corresponding recess 532 such that the flange of top portion 522 flares outwardly and extends into corresponding undercut 534.

Figure 9:
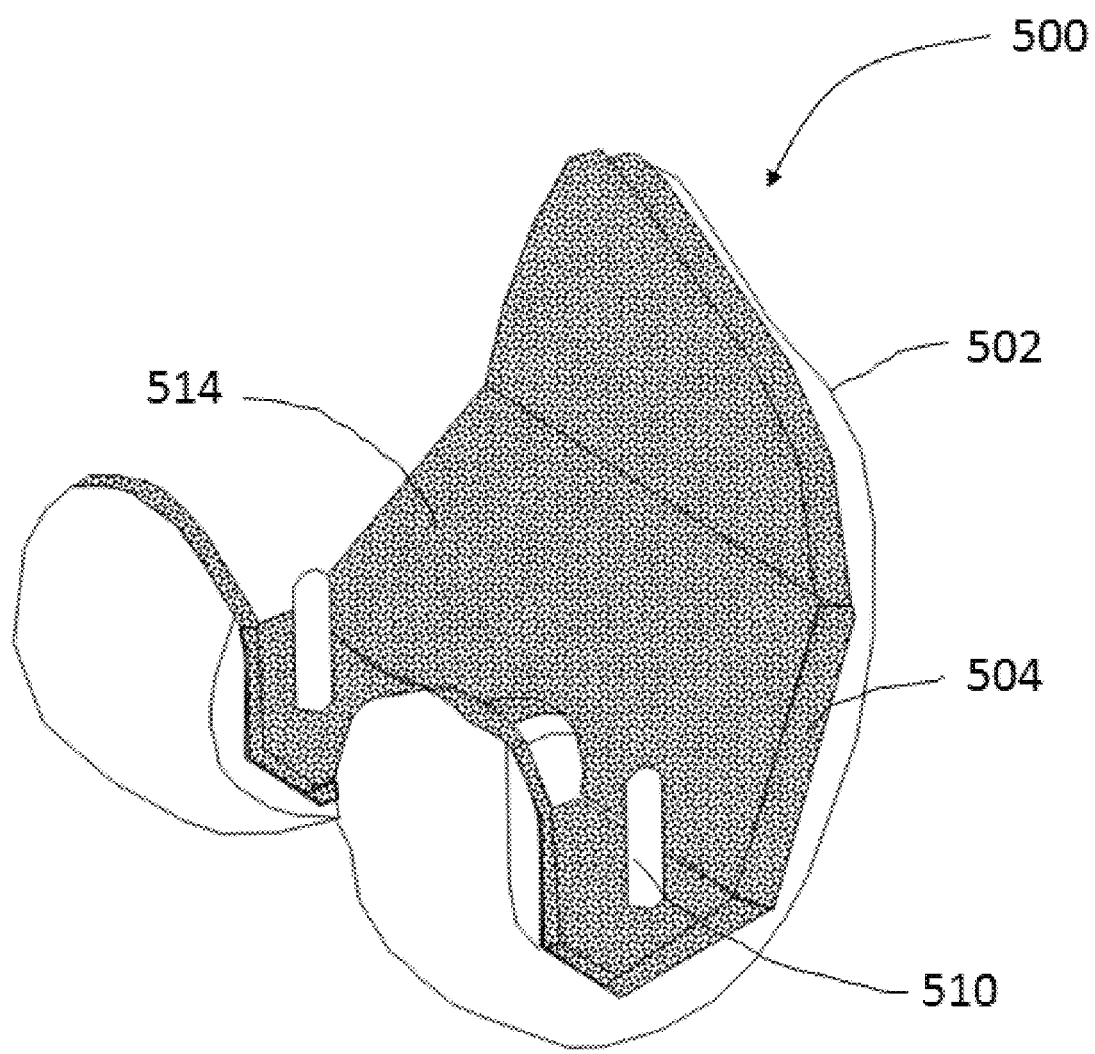
FIG. 9 is a perspective view of an implant in accordance with another embodiment.
Figure 10:
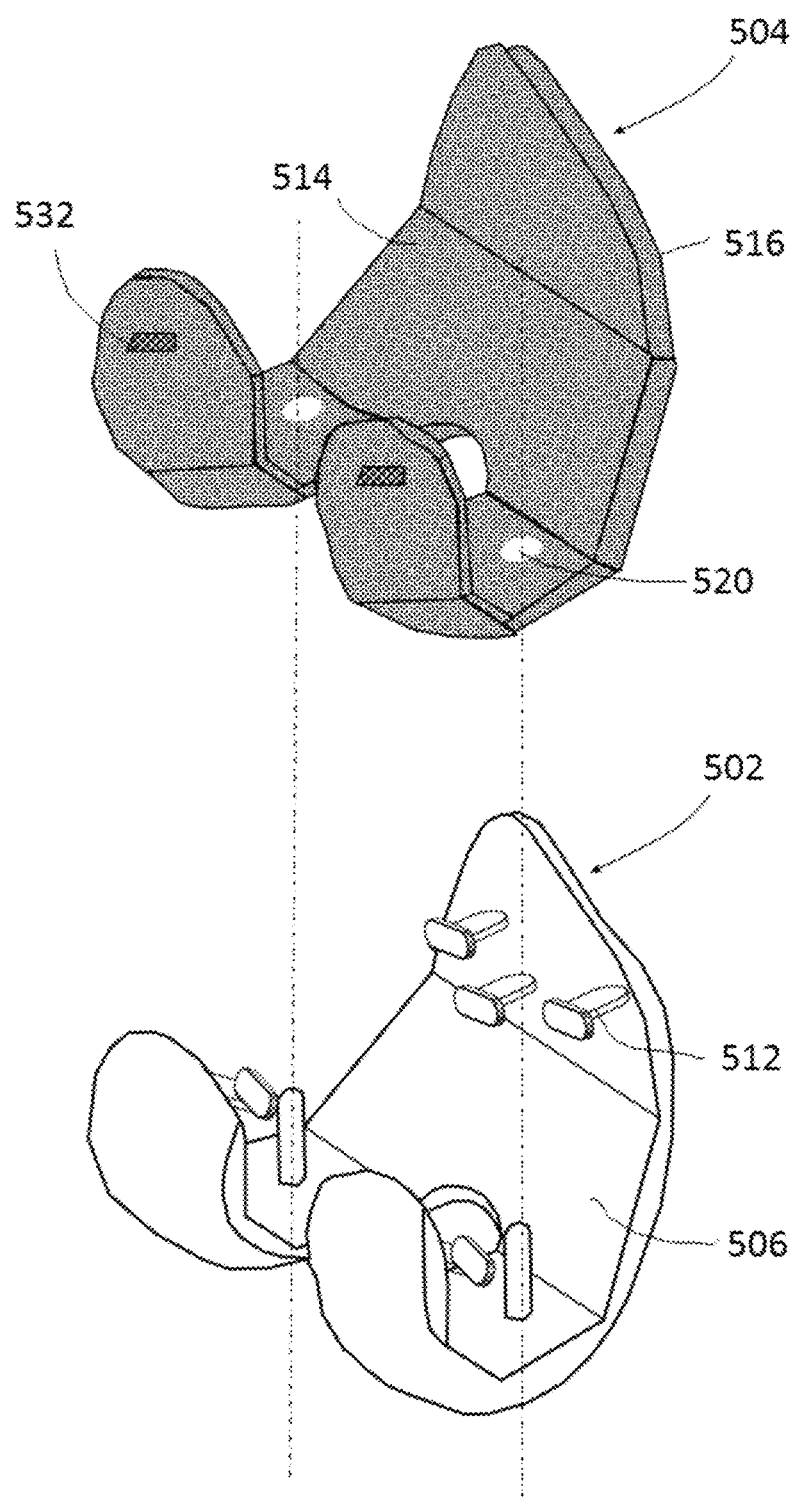
FIG. 10 is an exploded perspective view of the implant shown in FIG. 9.

In coupling body 502 to porous structure 504, bosses 512 on the posterior side are pressed into porous structure 504 as shown in FIG. 11B. Flexible body 502 is elastically deformed by the application of an external force, along direction 540 to allow bosses 512 on the opposite side, the anterior side, to be pressed into corresponding recesses 532. Resultant femoral implant 500 is shown in FIG. 9 (perspective view) and FIG. 11C (side elevation view).

While recesses 523 do not extend from top surface 514 to bottom surface 516 of porous structure 504, alternative arrangements may include holes extending completely through the porous structure such that corresponding top portions of the bosses rest on the top surface of the porous structure to prevent pullout or disassembly of the bosses from the porous structure and to secure the porous structure to the body. A flexible body configuration and method to facilitate fitting an outer body to an inner rigid body may be made in the manner disclosed in U.S. patent application Ser. No. 15/137,601, the disclosure of which is hereby incorporated by reference herein as if fully set forth herein. In this manner, body 502 may induce residual compressive stresses to porous structure 504 to further aid in the securement of the porous structure to the body. Alternatively, a plurality of porous structures as shown in FIG. 3 may be individually attached to the body with flanged bosses in the form or substantially in the form of bosses 512.

Outer body 102, 402, 502 may be, but is not limited to being, made of any polymer such as PEEK, carbon fiber reinforced PEEK, PAEK, UHMWPE, metals, ceramics, combinations of the foregoing, or other suitable materials that are biocompatible and possess sufficient strength and rigidity. The porous structure may be, but is not limited to, being made of any of titanium, titanium alloys, stainless steel, cobalt chrome alloys, tantalum and niobium or other suitable material.

As depicted in FIG. 12, an implant in accordance with an embodiment may be fabricated through fabrication process 600. In block 610, a body, which may be an outer body, is formed with bosses extending from an inner surface. Pressurized and molten PEEK or other suitable polymer material as described previously herein is injected into a mold configured to form the body. As best seen in FIG. 4A, bosses, such as but not limited to bosses 112, 412, 512 are molded simultaneously with the rest of the body. In this example, the bosses are integral with the body such that they are inseparable from the body.

In block 620, a three-dimensional porous structure with corresponding holes configured to receive the bosses of the body, such as but not limited to porous structures 104 204, 404, is then formed by additive manufacturing. In one example, the porous structure may be a titanium or other metallic foam fabricated by utilizing any of the following additive manufacturing processes: (1) beam overlap fabrication disclosed in U.S. Patent Publication No. 2004/0191106, (2) tessellated unit cell fabrication disclosed in U.S. Patent Publication No. 2006/0147332, (3) laser and e-beam polymer interdigitation disclosed in U.S. Patent Publication No. 2007/0142914, (4) conformal surfaces fabrication disclosed in U.S. Patent Publication No. 2013/0268085, or (5) mesh and chain mail fabrication disclosed in U.S. patent application Ser. No. 12/969,695, the disclosures of all of which are hereby incorporated by reference herein as if fully set forth herein. The porous structure may be but is not limited to being made as a single construct that covers substantially the entire body (as shown for example in FIG. 2 or FIG. 10), or composed of multiple segments that partially cover the body (as shown for example in FIG. 3).

Other suitable biocompatible materials as described above may also be used depending on the desired porosity of the porous structure.

In block 630, the porous structure is then assembled with the body. The bottom surface of the porous structure may be placed on the mating surface of the formed body such that a top portion of the boss protrudes through the porous structure and a bottom portion is within the hole, as in the example of FIG. 5A. When segmented porous structures are used, these structures may be selectively placed on the body, thereby avoiding the placement of a porous structure in areas of high deformation.

Each boss may be formed to have any profile to fit within a profile of a corresponding hole through a porous structure. Such corresponding bosses and holes may have, but are not limited to having, a profile of a circle, an oval, any polygon, a star, a cross, and a composite of these shapes.

In block 640, the body is secured to the porous structure by heat staking the bosses. A heated thermal tip, such as but not limited to thermal tip 126, may be used to melt the protruding top portion of the boss (e.g., FIGS. 5A, 6A, 8A). The melted top portion may fill a counterbore volume in a hole of the porous structure such that the top portion firmly secures the body to the porous structure upon solidifying (e.g., FIGS. 5B, 6B, 8B). The shape of the solidified top surface of the boss may be varied by adjusting any of the shape and the volume of the counterbore relative to the protruding top surface of the boss to obtain a desired surface finish. While the heat staking process described in this embodiment will result in the melted boss attaching with the porous structure upon cooling and solidifying, other securing methods may only require deforming the top surface of the boss. For example, the top surface of the boss may be deformed by heat and/or pressure to form an enlarged head such that the boss prevents the porous structure from detaching from the body.

Referring now to FIG. 13, an implant may be formed by fabrication process 700. In block 710, a flexible body is formed in substantially the same manner as the body is formed in block 610 of fabrication process 600. Multiple bosses, which may be but are not limited to being different sizes and shapes, may be molded simultaneously on a mating first surface of the body. The bosses may be integral to the body such that the bosses are inseparable from the body, and the bosses may have an enlarged top portion as in the example of FIGS. 11A-11C. The bosses may have different dimensions and different profiles including any of a circle, an oval, any polygon, a star, a cross and a composite of these shapes. In block 720, a porous structure is then formed in substantially the same manner as the porous structure is formed in block 620 of fabrication process 600. The porous structure may be provided with recesses into which the bosses may be pressed, as in the example of FIGS. 11A and 11B. Alternatively, holes that extend through the porous structure may be provided instead of the recesses, as described previously herein. As indicated in block 730, the body is secured to the porous structure by pressing the bosses into the corresponding recesses, as demonstrated in the example of FIGS. 11A-11C.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made and are encouraged to be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. An implant comprising:
a body having opposing first and second surfaces, the first surface having a boss extending outwardly therefrom, wherein the boss is integral with the body; and
a porous structure attached to the body and having a first porous surface that cooperates with the boss of the body to prevent pullout of the boss from the porous structure, wherein a second porous surface opposite the first porous surface contacts the first surface of the body when the porous structure is attached to the body.

2. The implant of claim 1, wherein the boss defines a longitudinal axis that extends at an oblique angle to the first surface to prevent pullout of the boss.

3. The implant of claim 1, wherein the porous structure comprises two or more porous segments.

4. The implant of claim 3, wherein each porous segment is planar.

5. The implant of claim 1, wherein the first surface is an inner surface of the body having one or more planar surfaces.

6. The implant of claim 1, wherein the body is at least partially flexible to facilitate the fixation of the porous structure to the body.

7. The implant of claim 1, wherein the body is made of a polymer and is at least partially flexible.

8. The implant of claim 1, wherein the body is made of any of PEEK, PAEK, and UHMWPE.

9. The implant of claim 1, wherein the porous structure is made of any of titanium, titanium alloys, stainless steel, cobalt chrome alloys, tantalum and niobium.

10. The implant of claim 1, wherein the boss does not extend above a top surface of the porous structure.

11. An implant comprising:
a body having opposing first and second surfaces, the first surface having a boss extending outwardly therefrom, the boss being integral with the body, wherein the boss has a first portion and a second portion wider than the first portion; and
a porous structure attached to the body and having a first porous surface that cooperates with the second portion of the boss of the body to prevent pullout of the boss from the porous structure, wherein a second porous surface opposite the first porous surface contacts the first surface of the body when the porous surface is attached to the body.

12. The implant of claim 11, wherein the second portion defines an end of the boss such that the second portion forms any of a dome stake, rosette stake and hollow stake with the top surface of the porous structure.

13. The implant of claim 11, wherein the porous structure includes at least one hole and a counterbore, and wherein the boss of the body extends through the hole, the second portion of the boss extending within the counterbore of the hole.

14. The implant of claim 11, wherein the porous structure has a recess to receive the boss to prevent pullout of the porous structure.

* * * * *